United States Patent [19]

Edgar

[11] Patent Number: 4,465,929

[45] Date of Patent: Aug. 14, 1984

[54] CALIBRATION STANDARD FOR INFRARED ABSORPTION GAUGE

[75] Inventor: Roger F. Edgar, Maldon, England

[73] Assignee: Infrared Engineering Limited, Essex, England

[21] Appl. No.: 413,151

[22] Filed: Aug. 27, 1982

[30] Foreign Application Priority Data

Jun. 18, 1982 [GB] United Kingdom .................. 8217789

[51] Int. Cl.$^3$ ............................................ G01D 18/00
[52] U.S. Cl. .................................. 250/252.1; 250/353
[58] Field of Search .............. 250/252.1, 338 PY, 338, 250/341, 353; 356/243

[56] References Cited

U.S. PATENT DOCUMENTS 3,478,210 11/1969 Janacek ................................. 250/428
4,082,950 4/1978 Chen ..................................... 250/343

FOREIGN PATENT DOCUMENTS 2055296 5/1972 Fed. Rep. of Germany ...... 356/243
56-63242 5/1981 Japan .
1055111 1/1967 United Kingdom .

Primary Examiner—Janice A. Howell
Assistant Examiner—Constantine Hannaher
Attorney, Agent, or Firm—Mason, Fenwick & Lawrence

[57] ABSTRACT

The calibration standard is attached to a sensing head of an infrared absorption gauge for the purpose of calibrating the gauge. The calibration standard includes spectrally selective absorption means having a spectrum closely resembling that of a substance to be measured, such as water sorbed onto a paper sample. The calibration standard also includes optical means for returning infrared radiation, which has passed through the absorption means, to the absorption gauge substantially along the same path as would normally be followed by the radiation reflected from the sample in the absence of the standard. The spectrally selective absorption means is preferably made of anhydrous material, such as glass containing a rare earth substance, or polypropylene, which is stable. The optical means may include diffusing means and a reflective plane. According to one arrangement, the calibration standard comprises a housing with a window at one end, a plurality of diffusing elements attached to a central portion of the window and a reflective plane spaced from the diffusing elements. The window and/or the diffusing elements and/or the reflective plane may comprise or include the spectrally selective absorption means. Various arrangements are described.

33 Claims, 6 Drawing Figures

CALIBRATION STANDARD FOR INFRARED ABSORPTION GAUGE

This invention relates to a calibration standard for an infrared absorption gauge. The calibration standard may be used, in particular, with gauges designed to measure moisture, but it may also be used with gauges for measuring other parameters, including sorbed substances and coatings or films.

Infrared absorption gauges operate by projecting near infrared radiation at two or more wavelengths onto a material to be measured, and by measuring the amount of this radiation collected and focused onto an infrared detector or detectors. From the relative amounts of received radiation at the several wavelengths is computed the moisture content or other desired parameter of the material. A typical gauge generally comprises a sensing head which houses the optical components and a detector, and an electronic unit which is usually, though not necessarily, separate. Calibration standards described herein, by way of examples of the invention, co-operate with the sensing head of such a gauge.

Calibration standards allow the stability and precision of an infrared absorption gauge to be checked from time to time. They also permit a calibration that has been established on one gauge to be transferred to other gauges and enable readjustment of an infrared absorption gauge to read correctly after one or more of its components has been disturbed, repaired or replaced.

Calibration standards are known, for example, from U.K. No. 1,055,111 and U.S. Pat. No. 3,478,210. Both of these references describe moisture gauge standards which use hydrated salts or inorganic compounds having at least one hydroxyl radical bound to a metallic element as hydroxide in order to simulate the infrared radiation absorption characteristics of a moist organic substance. In both cases, the calibration standard is in the form of a disc-shaped holder having a recess containing the reference standard material, such as the hydrated salt, the recess being covered by an infrared transmitting window. The holder is positioned adjacent a sample whose moisture content is to be determined and at the same level as the sample (ie with respect to a gauge detecting head which contains a source of infrared radiation for radiating the sample and a photoelectric cell arrangement for receiving the infrared radiation reflected from the sample.) For example, if the sample is a moving web of paper, the moisture content of which is to be determined, the disc-shaped holder, containing the standard reference substance, is situated in the plane of the moving web. During calibration, the head must be moved laterally, over the mounting web of paper, so as to cause the beam of radiation from the head to align with the reference standard, whereby the photoelectric cell arrangement receives radiation reflected from the standard so that the gauge may be calibrated. Such relative movement is clearly disadvantageous with regard to the expense and complexity of the necessary relocating mechanism, as well as to problems of alignment of the optical paths and wear in the mechanism. Moreover, it may be impossible, in some circumstances, to locate the holder containing the reference standard substance in a position that would normally be occupied by the sample material to be measured. In such a case, if the holder is located at a level between the sample and the detecting head, the angles of incidence and the distribution of radiation re-entering the detecting head from the standard reference substance will not match those from the sample material and the effectiveness of the standard will be reduced.

Calibration standards are also known from U.S. Pat. No. 4,082,950 and Patent Abstracts of Japan, Vol. 5, No. 122, Aug. 7, 1981, page 74–794 (JP-A-5663242). In the former reference, a calibration assembly comprises a ring-shaped holder which holds upper and lower circular glass plates, the faces of the upper plate being etched and the plates being separated by a layer of particulate material (either activated magnesium silicate gel or cross-linked dextran gel). This form of standard is of the reflectance type, wherein the infra-red radiation is incident on the standard and reflected therefrom onto the measurement part of infra-red radiation absorption gauge. When using such a standard to calibrate the gauge, the standard would normally be placed in the sample zone of the gauge and hence the standard would occupy the same position as that normally occupied by the sample in order to provide the same distribution of reflected radiation. This is clearly not a practical possibility where the sample is, for example, a conveyor belt which is transporting crushed iron ore at high speed and where it is necessary to calibrate the gauge from time to time. The latter reference describes a standard which also includes a ring-shaped holder holding a pair of glass plates that are spaced apart by a layer of material having an absorption band nearly the same as that of water. The material is made by mixing an organic compound with a mixture containing glass fibre, pigment and ash. Such a standard is also of the reflectance type and would be used in a similar fashion to that described above with regard to U.S. Pat. No. 4,082,950.

A primary object of the present invention is to avoid the problems and disadvantages of the prior art by providing a calibration standard for an infra-red absorption gauge which standard does not need to be located in the same position as a sample in the sample zone of the gauge.

Another object of the invention is to provide a calibration standard which can be easily fitted to, and removed from, the head of an infra-red absorption gauge, thereby avoiding any need to swing or tilt the head to view the standard.

A further object of the invention is to provide a calibration standard wherein infra-red radiation is returned to the infra-red absorption gauge, after passing through spectrally selective absorption means, substantially along the same path as that followed by the radiation from the sample zone to the gauge, in the absence of the standard.

A still further object of the invention is to provide a calibration standard which uses spectrally selective absorption means having an infra-red absorption spectrum resembling that of a substance (such as water) and which has long term environmental stability and requires no special protective housing.

The present invention seeks to overcome the latter problems by providing a calibration standard for an infrared absorption gauge, said gauge having a source of infrared radiation, an exit to enable said radiation to reach a sample zone and an entrance to transmit the radiation reflected from the sample zone whereby the amount of sorbed substance on the sample, located in the sample zone, can be measured, the calibration standard comprising an assembly which includes spectrally selective absorption means to receive infrared radiation from said exit when said calibration standard co-operates with said absorption gauge, said spectrally selective absorption means having an infrared absorption spectrum resembling that of the substance to be measured, and optical means to return infrared radiation, which has passed through said spectrally selective absorption means, to said entrance substantially along the same path as that followed by infrared radiation from the sample zone to said entrance in the absence of the calibration standard.

The optical means preferably comprises means for diffusing the infrared radiation and means (such as a reflective plane) for returning diffused radiation to the entrance of the absorption gauge. The arrangement is such that diffused infrared radiation, from which absorption components have been removed by the spectrally selective absorption means, is returned to said entrance at circularly symmetric angles of incidence substantially similar to corresponding angles of incidence of infrared radiation which would be reflected from a sample at a given sample distance from the infrared absorption gauge.

Preferably, in addition to the spectrally selective absorption means, spectrally unselective absorption means are provided in the assembly of the calibration standard, for absorbing infrared radiation over its spectral wavelength band, in order to reduce the amount of infrared radiation received by the absorption gauge from the calibration standard. The reduction is such as to simulate the amount of light which would normally be received by the gauge from the sample in the sample zone in the absence of the calibration standard. Suitably, the spectrally unselective absorption means absorbs about 70% of the light received by the calibration standard from the exit of the absorption gauge. A spectrally unselective absorption element may be made by coating a piece of glass with an infrafred radiation absorptive coating.

According to a preferred arrangement, an optical component or sub-assembly, comprising diffusing means as well as the spectrally selective absorption means, is located centrally of a window which receives the infrared radiation from the exit of the absorption gauge. The window may be either fully transmissive to the infrared radiation, or it may also include the spectrally selective absorption means. Preferably, the arrangement comprises a plurality of spectrally selective absorption means in order to increase the selective absorption of the particular components in the infrared spectrum of the selective absorption means. The diffusion/absorption component or sub-assembly is spaced from another component or sub-assembly which includes a reflective plane and preferably also further spectrally selective absorption means. In reflective plane reflects diffused radiation, from which the absorption components have been removed, onto the entrance of the absorption gauge (adjacent which are located radiation sensors, such as photoelectric cells). Various other arrangements are possible including different combinations of the window (which may either transmit all of the infrared radiation, or include the spectrally selective absorption means), the spectrally selective absorption means, the diffusing means, the reflective plane, and (if required) the spectrally unselective absorption means.

For example, combined spectrally selective absorption means and a reflective plane may be spaced from a diffusing element, or a series of spaced diffusing elements, attached to a central portion of an infrared radiation transmissive window. In diffused radiation which is not absorbed by the spectrally selective absorption means is reflected (by the reflective plane) onto a region of the window surrounding the diffusing element or elements. According to another arrangement, the window includes or is combined with spectrally selective absorption means to form an 'absorbing window', having the required infrared absorption spectrum, and one or more diffusing elements are located centrally of the 'absorbing window'. The infrared radiation initially makes a first pass through a central portion of the 'absorbing window' and is then reflected by a reflective plane, whereby the diffused radiation (from which the absorption components have already been removed on the first pass) make a second pass through an annular region of the 'absorbing window' surrounding the central region. In this case, the infrared radiation makes a double pass through the spectrally selective absorption means. According to another arrangement, an annular spectrally selective absorption element surrounds a diffusing element or elements. A central portion of an infrared radiation transmissive window passes infrared radiation through the diffusing element or elements and the diffused radiation is reflected onto the annular absorption element by a reflective plane. The radiation passing through the annular absorption element is then transmitted through an annular region of the window surrounding the diffusing element.

In any of these arrangements, ie where a diffusing element or elements are imaged in a reflective plane, the reflective plane is suitably located within the assembly of the calibration standard so that it is located at about one half of the normal operating distance between the infrared radiation exit of the absorption gauge and a plane which is normally occupied by the surface of the material being measured. Moreover, where more than one diffusing element is used, the diffusing elements are preferably spaced from one another, for example, by means of annular spacing rings.

The assembly of the calibration standard in all of the arrangements preferably comprises means for rigidly holding the absorption means (selective and unselective) and optical means in alignment whereby the calibration standard can be presented to, or withdrawn from a sensing head of an absorption gauge. In such an assembly, the reflective plane may be spaced from a fully transmissive, or partly transmissive window (eg a window including the spectrally selective absorption means) by one half of the normal operating distance between the gauge and the material being measured (as mentioned above). Regarding the prior art calibration standards mentioned above, these standards have another disadvantage in that hydrated salts lack long-term stability and have poor environmental resistance. Attempts to seal hydrated salts hermetically, so that their moisture content cannot change, are not always successful, especially at higher moisture levels where the hydrated salts are prone to deteriorate.

In preferred embodiments of the invention, the spectrally selective absorption means is preferably made of inherently anhydrous material which has an infrared absorption spectrum resembling that of the substance to be measured. The term "inherently anhydrous" is used herein to exclude substances, such as inorganic salts, containing water of crystalization, and substances which contain OH radicals, such substances having no inherent anhydrous property since their moisture content can change with time if they are not protected, e.g. by an hermetically sealed container.

For example, certain glasses containing rare earth materials exhibit a near infrared absorption spectrum resembling that of water. By way of another example, the inherently anhydrous spectrally selective absorption means could be made from a sheet of polymeric plastics material, such as polypropylene. Such anhydrous absorption means are advantageous in that they are chemically and mechanically stable compared with the hydrated salts mentioned above.

The invention may be embodied in a calibration standard which has the further advantages of being compact and capable of tolerating mechanical misalignment with respect to a sensing head of an infrared absorption gauge.

Embodiments of the invention will now be described with reference to the accompanying schematic drawings, in which.

Before describing calibration standards according to different embodiments of the invention, a brief description will first be given of materials which are suitable for making spectrally selective absorption means which simulates the spectrum of a substance (for example, water) which is normally sorbed on a sample placed in a sample zone of an infrared absorption gauge.

Figure 1:
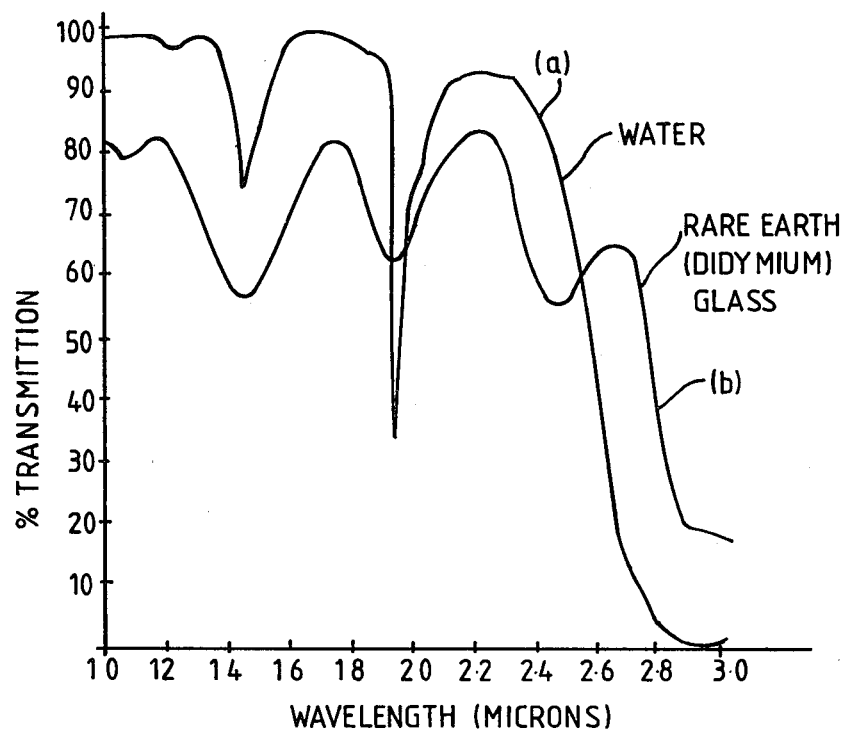
FIG. 1 shows near infrared spectra of a thin film of water and a rare earth glass.

Referring to FIG. 1, this shows the near infrared spectra of (a) thin film of water, and (b) of a rare earth glass of a type described as didymium glass. It can be seen that the spectrum of the didymium glass (b) shows infrared absorption bands at 1.48 and 1.96 microns, corresponding reasonably closely with the absorption bands of the water spectrum (a) at 1.45 and 1.94 microns. The water spectrum represents a layer of water approximately 90 microns thick and the didymium glass spectrum, a piece of glass about 3 mm thick. Thus, in this case, the selective absorption produced by a fairly small amount of water can be simulated by a conveniently thick sample of didymium glass. Such a piece of glass, having a suitable thickness, as determined experimentally, is an example of spectrally selective absorption means which may be used in a calibration standard according to an embodiment of the invention. The piece of glass may be used as a pure spectrally selective absorption element (and it may also serve as a window, having regard to the embodiment described below in which infrared radiation makes a double pass through the spectrally selective absorption element), or it may serve a double purpose, for example, where its major surfaces are ground in order to provide a diffusing effect.

If it were necessary to design a calibration standard for use with an infrared absorption gauge for measuring a coating of an organic adhesive and to use an absorption wavelength in the region of 2.3 microns, suitable spectrally selective absorption means could be made from a sheet of polymeric plastics, such as polypropylene. The thickness and possibly diffusing properties of the sheet of plastics is again selected for the required effect.

Whereas the absorption means or absorption elements described above are spectrally selective, ie they are provided for the purpose of specific absorption of infrared radiation at particular wavelengths, it is also preferably to provide spectrally unselective absorption means in order to reduce the amount of infrared radiation received by infrared absorption gauge in order to reduce the signal levels received by the detectors (eg photocells) to a value which is comparable with those that would be received from the substance or sample placed in the sample zone of the absorption gauge in the absence of the calibration standard.

For example, although there is no specific rule for the amount of infrared radiation which is unselectively absorbed, it has been found (in practice) that the use of spectrally unselective absorption means, which absorb about 70% of the infrared radiation over its whole spectral wavelength range, can provide optimum results. Such spectrally unselective absorption means may be made by coating a piece of glass, which transmits infrared radiation, with a coating which absorbs infrared radiation. Such a coating may be, for example, Inconel, chromium, or a similar vacuum deposited metal.

Generally speaking, the material selected for the spectrally selective absorption means must be spectrally similar to the substance to be measured by the infrared absorption gauge. Preferably also, the substance is chemically and mechanically stable and these are properties of the materials mentioned above.

Figure 2:
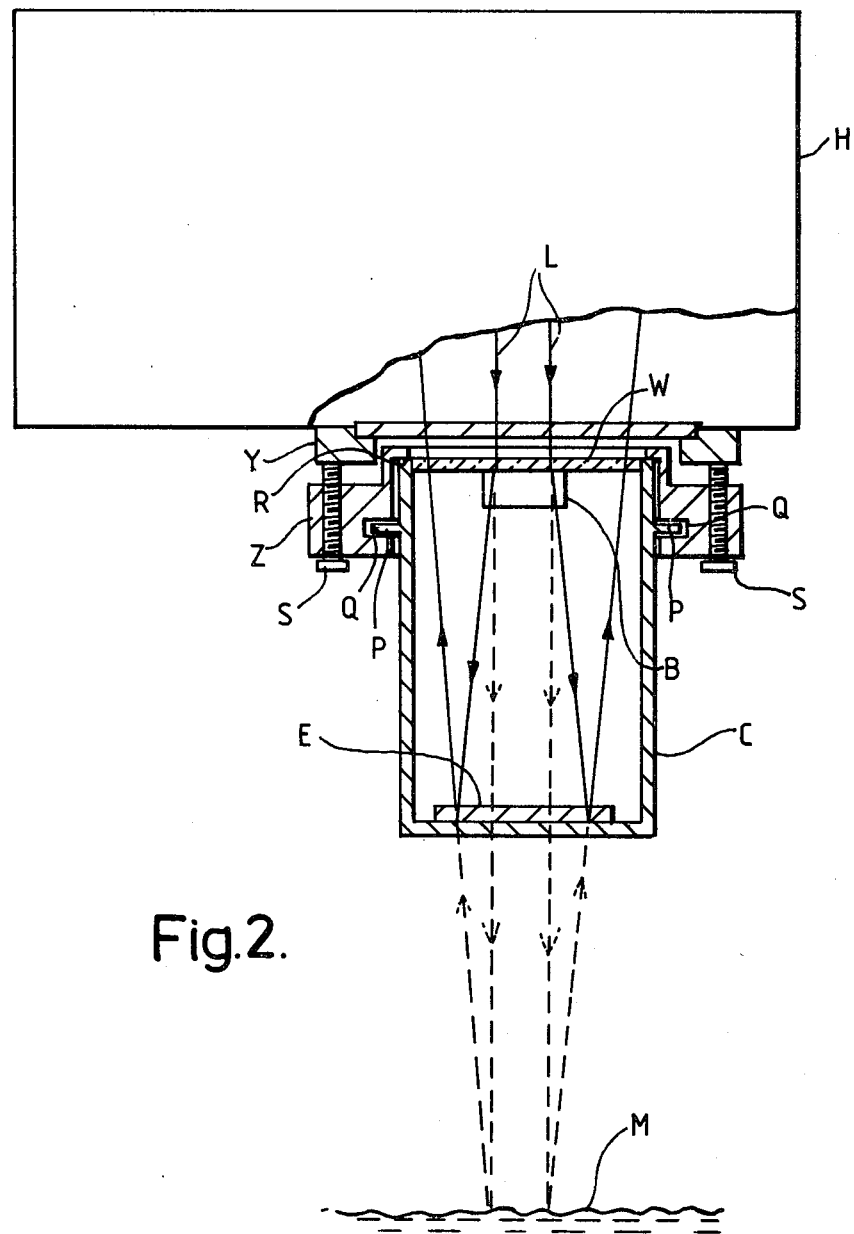
FIG. 2 shows a calibration standard according to one embodiment and means by which it is mounted on a sensing head of an infrared absorption gauge.

Referring now to FIG. 2, this schematically illustrates a calibration standard C according to one embodiment of the invention. The calibration standard C is attached to a sensing head H of an infrared absorption gauge. The construction and operation of such a gauge will be known to those skilled in the art so no detailed description will be given. In FIG. 2, the actual path taken by measurement infrared radiation beams L is shown by continuous lines, and the path that would be taken by these beams in the absence of the calibration standard (when removed from the head) is shown by the broken lines. On emerging from an exit of the sensing head H, beams of radiation L pass into the calibration standard C. The beams first pass through an infrared radiation transmissive window W (or a window W made of material having spectrally selective absorption as described above) and then through an optical component or sub-assembly B. For the moment, it may be assumed that the component B has the properties of optical diffusion and at least spectrally selective (and preferably also spectrally unselective) absorption. Component B therefore diminishes the intensity of beams L, but increases their divergence. These divergent beams then pass towards component E which, for the moment, may be assumed to have the properties of spectrally selective absorption and optical reflection from a plane surface. The reference to 'spectrally selective absorption' means that the absorption spectra of components B and E is similar to that of the material or sample which is to be measured by the infrared absorption gauge. This material or sample is designated M in FIG. 2. It may be, for example, water sorbed onto a web of paper which is moving continuously through a sample zone of the sensing head H.

In the absence of the calibration standard C, ie when it is removed from the head H, the measurement beams of infrared radiation L would follow the path shown by the broken lines whereby some of the radiation is reflected from the surface of the material M into the entrance of the sensing head H adjacent which are located photocells (not shown) for detecting the infrared radiation. The infrared radiation passing through this entrance lacks the components which have been absorbed by the material M. It can be seen, in FIG. 2, that the path of radiation reflected from component E (continuous lines) is the same as the path which would be followed by the radiation reflected from the material M in the absence of the calibration standard C. The optical arrangement of the calibration standard C is such as to produce this effect. One way of understanding this effect is to note that the component E produces a virtual image of the component D in a plane which is coincident with the material M to be measured. In this particular case, the optical arrangement is such that the component E is located at about one half of the distance between the region or exit from which the measurement beams emerge from the sensing head H and the material M to be measured. In this way, beams of radiation will take the same path and interact identically with the optical components and the radiation responsive detector or photocell assembly in the sensing head H. The optical arrangement may be considered as one wherein diffused radiation (from component B) is returned (by component E) to the window W at circularly symmetric angles of incidence substantially similar to corresponding angles of incidence of infrared radiation which would be reflected from the material M at a given sample distance from the sensing head H of the infrared absorption gauge. This arrangement greatly improves the performance of the calibration standard C compared with prior art calibration standards, because the detectors (eg photocells) used in the sensing head H commonly exhibits a non-uniform sensitivity and a non-uniform spectral response over their surface. Prior art calibration standards have not been able to meet this requirement, except when occupying the space normally occupied by the material M to be measured. This is clearly a major inconvenience when the infrared absorption gauge is used to make measurements on a moving production line, such as a moving web of paper.

With regard to the arrangement shown in FIG. 2, it will be apparent that to achieve the necessary coincidence of the paths of the beams of radiation re-entering the sensing head H from either the calibration standard C, or material M, the optical component E must be set at a normal angle to the mean direction in which the radiation beams L emerge from the sensing head H. Since errors in optical alignment and production tolerances lead to some variation in the direction of emerging beams L from one sensing head to another, provision is made to adjust the angle at which the calibration standard C is mounted on the sensing head H. An example of such an adjustable mounting will now be described with reference to FIG. 2. Annular ring Z is adjustably mounted to annular ring Y by adjusting screws S which permit adjustment of the angle between the arcs of the two rings by a small amount, for example 5°, in any direction. Annular ring Y is rigidly mounted to the body of sensing head H. Locating pins P are set into the cylindrical body of calibration standard C and a pair of spiral grooves Q are cut into the inner face of annular ring Z in the manner of a coarse screw thread. Thus, calibration standard C may be inserted into annular ring Z and gently rotated until pins P engage with spiral grooves Q. The calibration standard then screws into annular ring Z until its upper face locates against flange R.

To use the calibration standard, annular rings Y and Z are left permanently attached to the sensing head and adjusting screws S adjusted until the necessary coincidence of the paths of the beams of radiation is obtained with and without the calibration standard in place.

Figure 3:
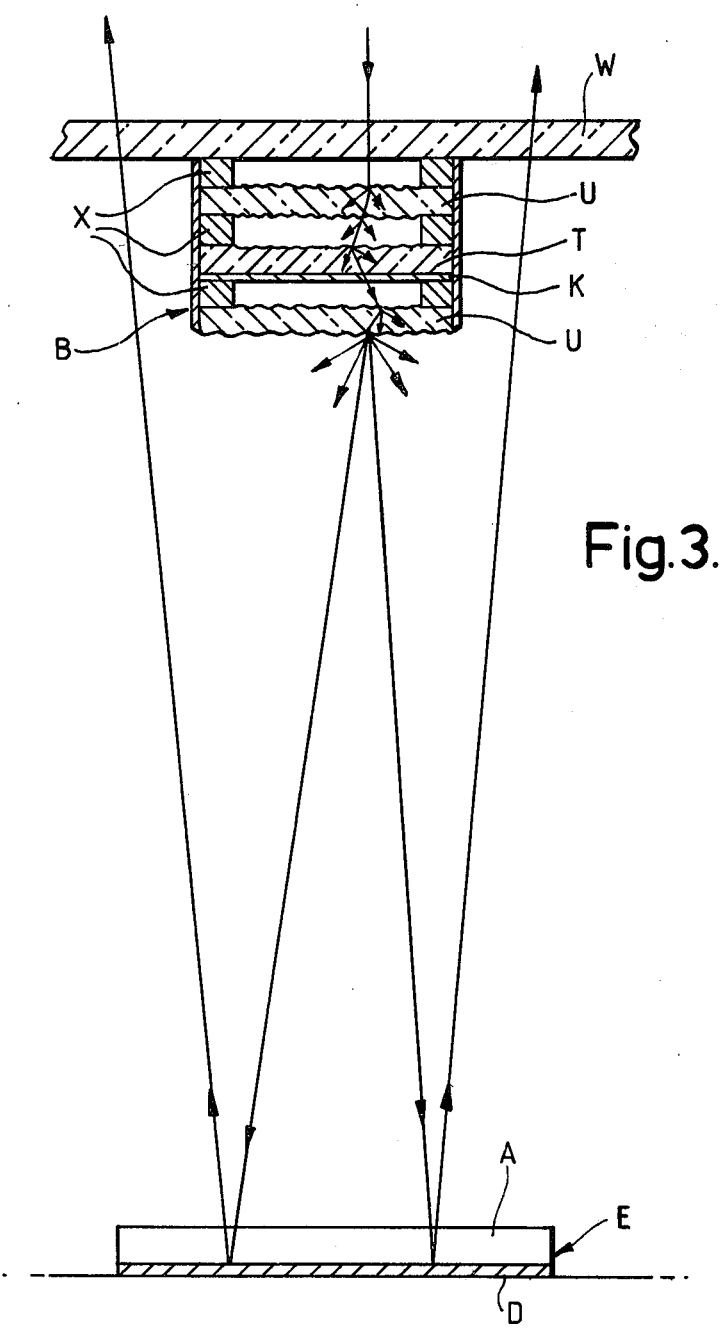
FIG. 3 illustrates the main parts of the calibration standard shown in FIG. 2 on a larger scale.

FIG. 3 shows the optical components B and E in greater detail. Component B has the properties of diffusion and both spectrally selective and unselective absorption.

In this example it comprises three circular optical elements, separated by annular spacer rings X. Optical elements U are flat glass discs, made of material such as didymium glass (ie which exhibits the required selective absorption), with both sides ground. Optical element T is a flat glass disc (also made of material with spectrally selective absorption—such as didymium glass) having one side ground and the other coated with a coating K which has a spectrally unselective absorption of infrared radiation. It will be apparent that other configurations and materials may be used to produce the necessary combination of diffusion and spectrally selective and unselective absorption. However, if ground glass is used, several ground surfaces will be necessary to produce sufficient diffusion. The spacers X improve the diffusion efficiency and lead to a divergent beam of radiation which is more uniform over its surface. One or more of the optical elements may be made of the glass or material mentioned above, which exhibits an absorption spectrum resembling that of the substance to be measured or they may be made of material which transmits infrared radiation. The selection of such elements depends on the intended use of the gauge with a given substance to be measured. The spectrally unselective infrared radiation adsorptive coating K of element T, may be Inconel, Chromium, or a similar vacuum deposited metal.

The upper annular spacer ring X permits the assembly to be fastened to the protective window W. Although alternative mounting methods can obviously be used, it is convenient to stick the assembly together and to secure it to the window using an adhesive such as an epoxy resin. The outer cylindrical surface of the subassembly or component B is preferably painted black, or otherwise treated, to prevent the egress of stray radiation. In order to reduce sensitivity to small errors in alignment, the assembly should be slightly larger in diameter than the beams or radiation emerging from the sensing head H. The optical component E has the properties of optical reflection from a plane surface and spectrally selective absorption (ie with the required spectral response). Component E comprises a plane circular disc A with one side D metallised. The disc A may be made of the glass or material exhibiting an absorption spectrum resembling that of the substance to be measured. The metallised layer D will usually be provided with a protective backing and then can be either stuck or mechanically secured in the calibration standard. The diameter of this disc should be greater than the diameter of the beams of radiation that are received at the sensing head H from the material M when the calibration standard C is not in use.

The protective window W may be made of the glass or material exhibiting an absorption spectrum resembling that of the material to be measured.

The performance of the calibration standard may be improved by applying anti-reflection coatings to the surfaces of the protective window W.

It will be apparent that the glass or other material exhibiting the absorption spectrum similar to that of the product to be measured may be located in the diffusion-/absorption sub-assembly B, the reflection/absorption sub-assembly E, or used as the protective window W, or any combination thereof. Although the last alternative will rarely be selected, the choice will depend on the particular application and the glass or material selected. In the case of a moisture calibration standard, where a rare earth glass is selected, the diffusion/absorption sub-assembly B shown in FIG. 3 may be most practical for a standard representing a low moisture level in a material, since the radiation beam only passes through it once.

For a high moisture standard however, the reflection-/absorption sub-assembly E shown in FIG. 3 may be a better choice since the radiation beam passes through it twice.

Figure 4:
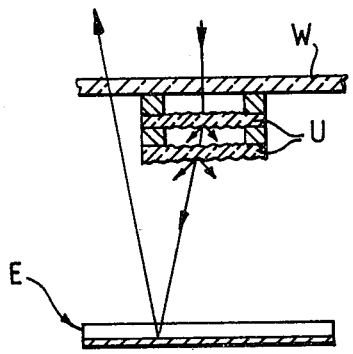
FIGS. 4-6 illustrate further respective embodiments.
Figure 5:
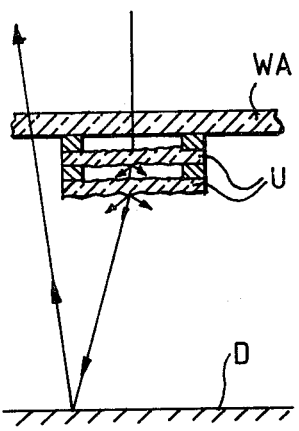
Figure 6:
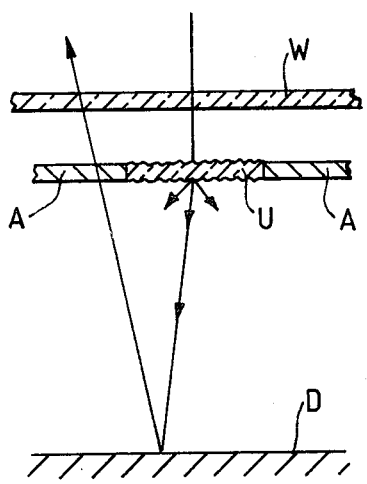

Apart from the spectral absorption characteristic of the substance to be measured, there is a need for overall absorption so that the intensities of the beams received at the detector from the calibration standard C are similar to those received from the material to be measured. The absorptive coated element T, K in the diffusion/absorption sub-assembly B is selected to achieve this. The effectiveness of the calibration standard C is increased by taking care to design and construct it with a circularly symmetric optical system, which makes it insensitive to rotation, and, in the particular embodiment described here, insensitive to wear in the mounting system. FIGS. 4-6 schematically illustrate further respective arrangements.

In FIG. 4, the window W transmits infrared radiation to a pair of spaced diffusing elements U. Some of the diffused radiation is reflected from an absorption/reflective element E (similar to that shown in FIG. 3) back through the window W into the entrance of the absorption gauge (not shown).

In FIG. 5, a window WA, which is made of material having the required absorption spectrum, transmits radiation through a pair of diffusing elements U. A reflective plane D reflects some of the diffused radiation back through the window WA.

In FIG. 6, the window W transmits radiation through a diffusing element U and diffuse radiation is reflected, from reflective plane D through an annular element A, made of the material having the required absorption spectrum. Radiation then passes out through window W.

In either FIG. 4 or 6, the window W may include spectrally selective absorption means to increase the absorption of the required components in the infrared spectrum.

Absorption elements with different spectrally selective absorption spectra may be used in conjunction with one another, (either in contact, or spaced apart) to provide a combined spectral response (e.g. to provide more absorption peaks) by way of an example, optical component B may include spectrally selective absorption elements made of polypropylene and optical E may include a spectrally selective absorption element made of didymium glass.

I claim:

1. A calibration standard for an infrared absorption gauge, said gauge having a source of infrared radiation, an exit to enable said radiation to reach a sample zone and an entrance to transmit the radiation reflected from the sample zone whereby the amount of sorbed substance on a sample, located in the sample zone, can be measured, the calibration standard comprising an assembly which includes spectrally selective absorption means to receive infrared radiation from said exit when said calibration standard co-operates with said absorption gauge, said spectrally selective absorption means having an infrared absorption spectrum resembling that of the substance to be measured, and optical means to return infrared radiation, which has passed through said spectrally selective absorption means, to said entrance substantially along the same path as that followed by infrared radiation from the sample zone to said entrance in the absence of the calibration standard.

2. A calibration standard according to claim 1, wherein the optical means comprises means for diffusing the infrared radiation and means for returning diffused radiation to the entrance of the absorption gauge.

3. A calibration standard according to claim 2, wherein the means for returning the diffused radiation to said entrance comprises a reflective plane.

4. A calibration standard according to claim 1, wherein the optical means is located, within said assembly, so that it is positioned at about one half of the normal operating distance between said exit of the absorption gauge and said sample zone.

5. A calibration standard according to claim 1, wherein said assembly comprises a housing having a window at one end to receive the infrared radiation from the exit of the absorption guage and having a reflective plane adjacent its other end for returning radiation to said entrance of the absorption guage, said spectrally selective absorption means being provided in said assembly to intercept the radiation on its path from said exit in said entrance, and diffusing means being provided to diffuse the radiation passing through said window onto said reflective plane.

6. A calibration standard according to claim 5, wherein said housing is supported by means enabling the housing to be tilted when fitted to the exit of said guage.

7. A calibration standard according to claim 6, wherein said diffusing means is located adjacent a central portion of said window, the diffused radiation reflected from said reflective plane passing through a region of the window surrounding said central portion.

8. A calibration standard according to claim 7, wherein said diffusing means comprises a plurality of spaced diffusing elements.

9. A calibration standard according to claim 8, wherein the diffusing means and the spectrally selective absorption means are structured as a sub-assembly or optical component which is attached to a central portion of said window.

10. A calibration standard according to claim 9, wherein said spectrally selective absorption means and said reflective means are structured or combined as a sub-assembly or optical component.

11. A calibration standard according to claim 10, wherein said window comprises said spectrally selective absorption means.

12. A calibration standard according to claim 11, wherein said spectrally selective absorption means is made of anhydrous material.

13. A calibration standard according to claim 12, wherein said anhydrous material is made of glass containing a rare earth substance.

14. A calibration standard according to claim 12, wherein said anhydrous material is made of polypropylene.

15. A calibration standard according to claim 14, further including spectrally unselective means for absorbing the infrared radiation in its band width in order to reduce the amount of infrared returned by said optical means.

16. A calibration standard according to claim 15, wherein said unselective absorption means absorbs about 70% of the infrared radiation.

17. A calibration standard according to claim 15, wherein the absorption means is made of a radiation transmissive material having a radiation absorptive coating.

18. A calibration standard according to claim 17, wherein said radiation transmissive material comprises said spectrally selective absorption means.

19. A calibration standard according to claim 18, wherein said material is glass in the form of a disc having one side ground and the other side coated with said infrared radiation spectrally unselective absorptive coating.

20. A calibration standard for an infra-red absorption gauge comprising a window for transmitting infra-red radiation, diffusing means for diffusing the infra-red radiation, a reflective plane, and spectrally selective absorption means having an infra-red absorption spectrum resembling that of the substance to be measured, said spectrally selective absorption means being arranged to transmit the infra-red radiation therethrough, and said reflective plane being spaced from said diffusing means and arranged to return the infra-red radiation to said window.

21. A calibration standard according to claim 20, comprising a housing having the window at one end, said reflective plane being adjacent the other end of the housing.

22. A calibration standard according to claim 20, wherein said diffusing means is located adjacent a central portion of said window, the diffused radiation reflected from said reflective plane passing through a region of the window surrounding said central portion.

23. A calibration standard according to claim 20, wherein said diffusing means comprises a plurality of spaced diffusing elements.

24. A calibration standard according to claim 20, wherein said diffusing means and the spectrally selective absorption means are structured as a sub-assembly or optical component which is attached to a central portion of said window.

25. A calibration standard according to claim 20, wherein said spectrally selective absorption means and said reflective plane are structured or combined as a sub-assembly or optical component.

26. A calibration standard according to claim 20, wherein said window comprises said spectrally selective absorption means.

27. A calibration standard according to claim 20, wherein said spectrally selective absorption means is made of inherently anhydrous material.

28. A calibration standard according to claim 27, wherein said anhydrous material is made of glass containing a rare earth substance.

29. A calibration standard according to claim 27, wherein said anhydrous material is made of polypropylene.

30. A calibration standard according to claim 20, wherein spectrally unselective means are also provided for absorbing the infra-red radiation in its bandwidth in order to reduce the amount of infra-red radiation returned to said optical window.

31. A calibration standard according to claim 30, wherein said unselective absorption means absorbs about 70% of the infra-red radiation.

32. A calibration standard according to claim 20, wherein said spectrally selective absorption means is made of a radiation transmissive material having the spectrally selective absorption property.

33. A calibration standard according to claim 32, wherein said material is glass in the form of a disc having one side ground and the other side coated with an infra-red radiation spectrally unselective absorptive coating.

* * * * *